US012751916B2

(12) United States Patent
Scherliess et al.

(10) Patent No.: US 12,751,916 B2
(45) Date of Patent: Oct. 6, 2026

(54) POWDER FORMULATIONS FOR INHALATION

(71) Applicant: Christian-Albrechts-Universität zu Kiel, Kiel (DE)

(72) Inventors: Regina Scherliess, Kiel (DE); Simon Stefan Bock, Kiel (DE)

(73) Assignee: Christian-Albrechts-Universität zu Kiel, Kiel (DE)

(*) Notice: Subject to any disclaimer, the term of this patent is extended or adjusted under 35 U.S.C. 154(b) by 898 days.

(21) Appl. No.: 17/783,536

(22) PCT Filed: Dec. 2, 2020

(86) PCT No.: PCT/EP2020/084271
§ 371 (c)(1),
(2) Date: Jun. 8, 2022

(87) PCT Pub. No.: WO2021/115877
PCT Pub. Date: Jun. 17, 2021

(65) Prior Publication Data

US 2022/0401358 A1 Dec. 22, 2022

(30) Foreign Application Priority Data

Dec. 10, 2019 (DE) ......................... 102019219277.7

(51) Int. Cl.
*A61K 9/00* (2006.01)
*A61M 15/00* (2006.01)

(52) U.S. Cl.
CPC ....... *A61K 9/0075* (2013.01); *A61M 15/0008* (2014.02); *A61M 15/005* (2014.02)

(58) Field of Classification Search
CPC ............ A61K 9/0075; A61M 15/0008; A61M 15/005; A61M 2202/064
See application file for complete search history.

(56) References Cited

U.S. PATENT DOCUMENTS

2001/0027790 A1* 10/2001 Gieschen .......... A61M 15/0008 128/200.22

FOREIGN PATENT DOCUMENTS

EP 2526990 A2 11/2012
WO 95/03846 2/1995

OTHER PUBLICATIONS

Hugh D.C. Smyth and Anthony J. Hickey; Carriers in Drug Powder Delivery Implications for Inhalation System Design Am J Drug Deliv 2005; 3 (2): 117-132; 1175-9038/05/0002-0117/$34.95/0 (Year: 2005).*

Melvin Wostry; Complex carrier particles for respiratory drug delivery analysed with sequentially built DEM-simulation models; https://doi.org/10.1016/j.ijpharm.2025.126081 (Year: 2025).*

Hickey, Anthony, "Complexity in Pharmaceutical Powders for Inhalation: A perspective", KONA Powder and Particle Journal, 2018, No. 35, pp. 3-13.

Renner, et al., "Nano- and Microstructured model carrier surfaces to alter dry powder inhaler performance", International Journal of Pharmaceutics, 2017, vol. 518, pp. 20-28.

International Search Report from the corresponding International Patent Application No. PCT/EP2020/084271, dated Feb. 16, 2021.

International Preliminary Report on Patentability from the corresponding International Patent Application No. PCT/EP2020/084271, dated May 17, 2022.

* cited by examiner

*Primary Examiner* — Robert A Wax
*Assistant Examiner* — Andre Mach
(74) *Attorney, Agent, or Firm* — Greer, Burns & Crain, Ltd.; Steven P. Fallon

(57) ABSTRACT

The invention relates to powdered pharmaceutical formulations which, in addition to carrier particles and particulate active ingredient which preferably adheres to the surface of the carrier particles, contains a mixing element, wherein the formulation fluidized in the carrier gas stream can contain the mixing element. Preferably, the powdered pharmaceutical formulation is packaged as a single dose, for example filled into a container as a single dose, for example in a capsule. The mixing element has a size of at least 1 mm to 10 mm in a first dimension and a size of at least 50% of the size it has in the first dimension in the other two dimensions.

15 Claims, 3 Drawing Sheets

POWDER FORMULATIONS FOR INHALATION

Figure 1:
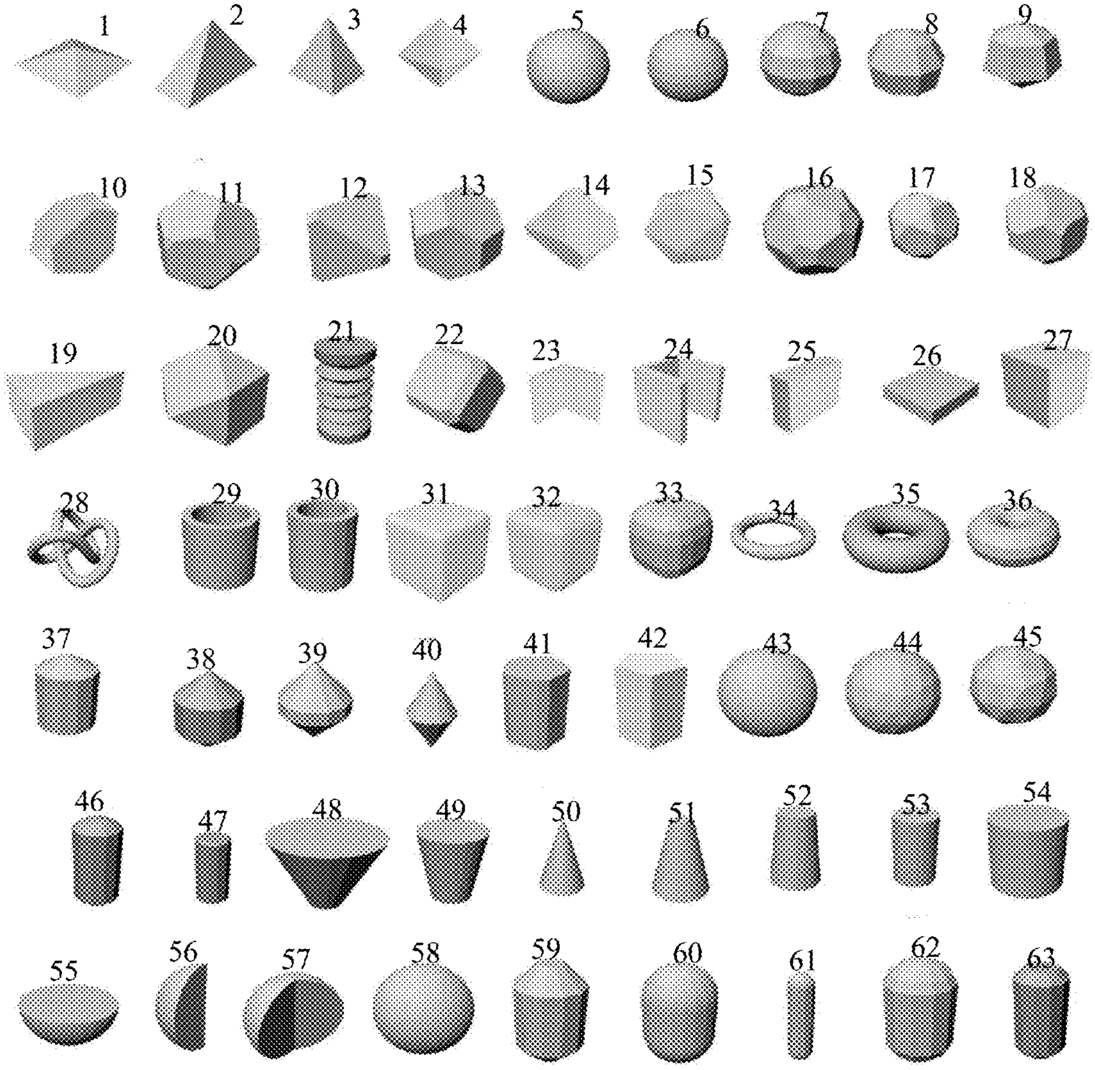
Figure 1:
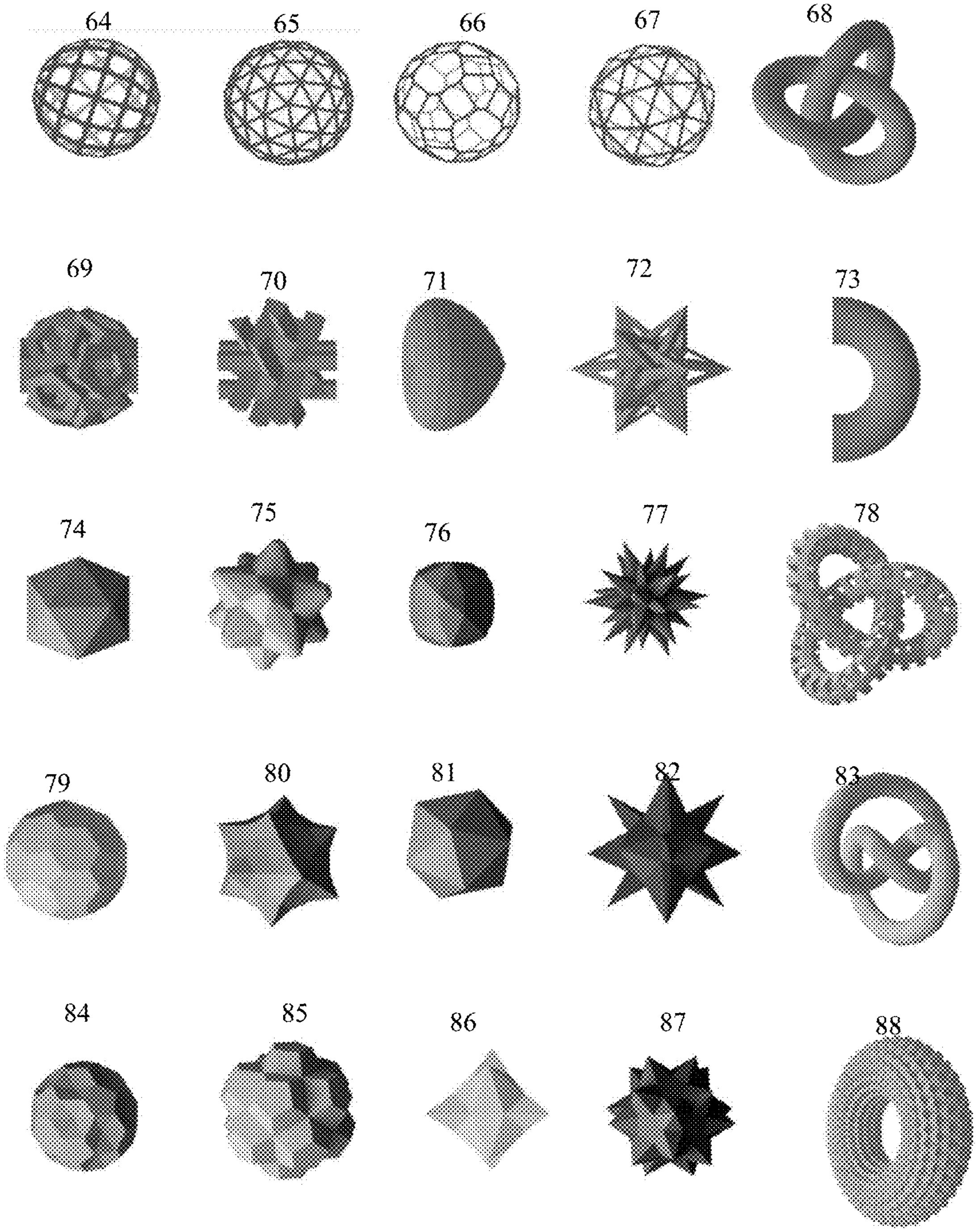
Figure 1:
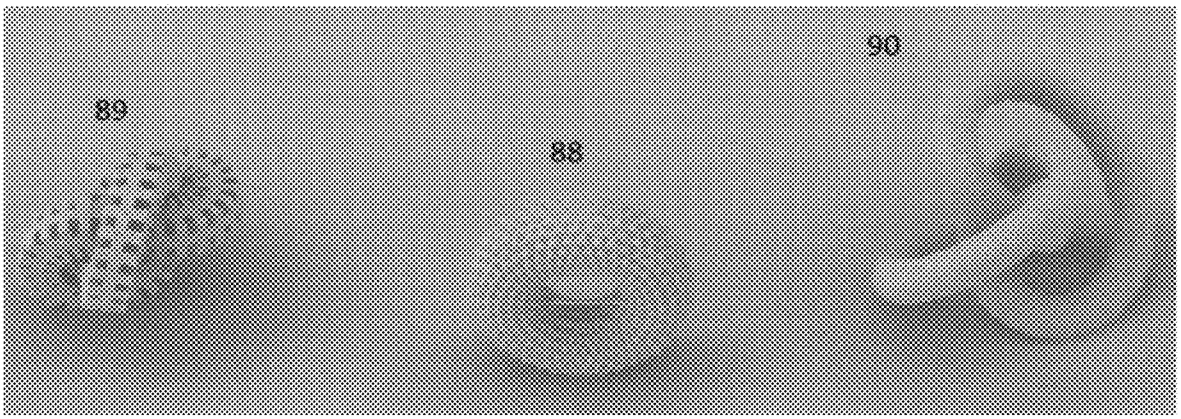

The present invention relates to powdered pharmaceutical formulations containing a particulate active ingredient and carrier particles to which the active ingredient adheres preferably only superficially, and to a process for producing such formulations. The formulations are characterized in that they contain a mixing element which is freely movable in the formulation and forms a dispersing aid for the particulate active ingredient and the carrier particles. In an alternative to the mixing element being included in the formulation, the mixing element may be arranged in a section of the flow channel of an inhaler, e.g. freely movable in a chamber through which carrier gas and powdered pharmaceutical formulation flow. The invention also relates to the mixing element and to a method of producing it, and further to preferred carrier particles and methods of producing them.

The mixing element has the advantage of producing a larger proportion of fine particles in the carrier gas from a powdered formulation, the fine particles having a size suitable for penetration into the lungs of, for example, 5 μm or less, when the formulation is swirled by means of a carrier gas, e.g. when a particle cloud is generated during inhalation.

STATE OF THE ART

Hickey, A., KONA Powder and Particle Journal 35 (2018) 3-13 for inhalation describes powdered pharmaceutical formulations for inhalation comprising as carrier particles lactose crystals, e.g. ground and sieved, and adhering thereto separately spray-dried or micronized active ingredient.

Renner et al, International Journal of Pharmaceutics 20-29 (2017) describe the aerodynamic behavior of interactive powder mixtures with glass spheres as carrier particles, which served as a model for carrier particles in powdered formulations with separately spray-dried active ingredient that readily adhered superficially to these carrier particles by mixing.

OBJECT OF THE INVENTION

The invention has the object of providing an alternative powdered pharmaceutical formulation and a process for its production. Preferably, the formulation is intended to produce as high a proportion as possible of particulate active ingredient of an aerodynamic particle size of at most 5 μm during distribution, in order to make the active ingredient particles inhalable or respirable. A further object lies in the provision of a mixing element suitable for fluidizing particulate active ingredient of a particle size of maximum 5 μm, in particular from a powdered pharmaceutical formulation in the carrier gas stream, and in the provision of a production process for such mixing elements.

DESCRIPTION OF THE INVENTION

The invention achieves the object by the features of the claims and, in particular, by a powdered pharmaceutical formulation which, in addition to carrier particles and particulate active ingredient, which preferably adheres to the surface of the carrier particles, optionally contains a mixing element, wherein the formulation fluidized in the carrier gas stream can contain the mixing element. The carrier particles preferably have one and the same shape and size, so that the carrier particles are uniform in shape and size.

Preferably, the powdered pharmaceutical formulation is packaged as a single dose, e.g., filled as a single dose in a container, e.g., in a capsule. Alternatively, the formulation consisting of particulate active ingredient and of carrier particles may be contained in a reservoir in the inhaler from which a single dose is divided prior to dispersion or fluidization.

The mixing element has a size in a first dimension of at least 1 mm, preferably of at least 1.5 mm or of at least 2 mm, e.g. up to 10 mm or up to 9 mm or up to 8 mm or up to 7 mm, and in the other two dimensions a size of at least 50%, preferably at least 60%, at least 70%, at least 75%, at least 80% or at least 90% of the size it has in the first dimension.

Generally preferred, the formulation has the active ingredient in particle sizes of the individual particles of 5 μm or less, wherein particles in the formulation may be agglomerated, e.g. adhering to the surface of carrier particles.

Preferably, the mixing element contained in the powdered pharmaceutical formulation has walls disposed about a cavity and having at least one aperture open to the cavity. The walls encompass the at least one aperture and open up a cavity between them, such that the cavity is open through the at least one aperture. Preferably, the mixing element has walls disposed around the cavity the walls having at least two apertures disposed on opposing walls and open to the cavity. The walls of the mixing element have, between their outer surface and the cavity, a thickness of, for example, at most 20% or of at most 15% or of at most 10% of the size of the mixing element in this dimension. Opposite to the cavity the walls may have on their surfaces a total area of at most 50%, at most 40%, at most 30% or at most 20% or at most 10% of the total area of the at least one aperture opened up by the walls. Therein, the walls may together take up a total area, determined with respect to the cavity, which is at most 50% of the area spanned by the at least one aperture, so that the walls cover a smaller proportion of the cavity than the at least one recess spans across the cavity.

Optionally, the mixing element may have walls that allow rolling, in particular continuous rolling, along inner surfaces of a container, which may be a dispersion chamber or fluidization chamber, e.g. in the flow path or flow channel of an inhaler, or a storage container. The walls of the mixing element may be convexly curved, for example, on their surfaces opposite the cavity. Therein, the surfaces of the walls opposite the cavity, which form the outer surfaces of the walls and respectively of the mixing element, can be formed continuously or in sections. The continuously formed convexly curved surfaces may extend, for example, over at least ¼, ⅓ or ½ of the circumference.

This embodiment of the mixing element has been shown to cause higher fluidization of particles smaller than 5 μm when the powdered composition is swirled with a carrier gas, for example, compared to fluidization of an otherwise identical formulation without a mixing element. The higher fluidization of small particles is currently attributed to the dispersing effect of the mixing element on the formulation.

Therein, the mixing element may have walls formed by one or by at least two interconnected wall sections, each closed in on itself around an aperture, which extend in at least two planes lying, for example, at an angle of 45° to 90° to one another.

Alternatively, the mixing element may be solid with a self-contained surface of, for example, of a sphere, of a pyramid, of a cylinder, of a three-dimensional oval, of a cuboid, of a cube, of a cone, of a truncated cone, or of a polyhedron. Preferably, a solid mixing element has protrusions. For example, protrusions may terminate in a curved plane that allows the mixing element to roll along interior surfaces of a storage container. For example, the ends of the projections may form portions of a curved plane, respectively may form support points on which the mixing element rolls along the inner surface of a storage container.

It has been shown that a mixing element increases the proportion of fine particles of a maximum size of 5 μm that pass from the pharmaceutical formulation into the carrier gas by means of a carrier gas. The mixing element leads to an increase in the content of fine particles of a maximum size of 5 μm during fluidization of the pharmaceutical formulation in the carrier gas and therefore to increased entry of such particles into the lungs during inhalation. Preferably, the mixing element leads to the fluidization of fine particles, e.g. of a size of at maximum 4 μm, of at maximum 3 μm or of at maximum 2 μm, which can be inhaled into the peripheral regions of a lung.

Preferably, the mixing element is produced from a hardening mass by means of an additive manufacturing process, which is also generally known as a 3D printing process. Alternatively, mixing elements can be produced from a precursor mass by controlled radiation-induced curing, e.g. melt solidification or polymerization, which is also generally known as photopolymerization or laser lithography, respectively.

Mixing elements can, for example, be made of pharmaceutically acceptable plastic that is biologically resistant or that is biodegradable.

Biodegradable plastic is e.g. polylactide, polyglycolide, polylactide-co-glycolide (PLGA). A biologically resistant plastic is e.g. EVA or PMMA.

Preferably, the carrier particles of the formulation have a uniform size of at maximum 500 μm e.g. 50 to 500 μm or up to 400 μm or up to 350 μm in the longest extension, and a uniform shape. Therein, a uniform shape is generally an identical three-dimensional shape in each case. It has been shown that a uniform size and shape of the carrier particles enhances fluidization of the carrier particles and of the active ingredient that can adhere to the carrier particles by a gas stream and/or enhances the release of particulate active ingredient from the carrier particles within the respiratory tract.

The carrier particles are preferably also produced by means of an additive manufacturing process, e.g. by a 3D printing process or by photopolymerization.

The carrier particles preferably consist of material that can be degraded by a human body, e.g., after introduction of carrier particles into the upper respiratory tract or lungs. Examples of material of which carrier particles may consist include polylactide, polyglycolide, polylactide-co-glycolide (PLGA), sugars, in particular glucose and lactose, sugar alcohols, in particular mannitol, cellulose, cellulose derivatives, e.g. hydroxypropyl cellulose, hydroxyethyl cellulose, hydroxypropylmethyl cellulose, gelatine, alginate, agarose, carrageen, and mixtures of at least two of these.

The carrier particles preferably have uniformly the same shape and the same size. The shape may be one as described with reference to the mixing element, but with the size of a maximum 500 μm, e.g. 50 to 300 μm, in each dimension. Preferably, the carrier particles having the same size and shape, respectively having the identical shape are produced by an additive manufacturing process, in particular by means of a photolithographic process or by means of a 3D printing process.

The invention also provides an inhaler having a mixing element contained in the flow path thereof, e.g., in a dispersion chamber therein. Therein, a formulation of carrier particles and active ingredient is brought into contact with the mixing element in the section of the flow path in which the mixing element is contained. This section of the flow path may be, for example, its dispersion chamber. The mixing element is generally free to move in the section of the flow path and is retained, for example, by an outlet opening having a cross-section smaller than the mixing element.

In general, the active ingredient can be a combination of at least two active ingredients.

Preferably, the aerodynamic size of particles is determined using Apparatus E according to European Pharmacopeia 9.0.

The invention is now described in more detail by way of an example and with reference to FIG. 1, which shows exemplary shapes for mixing elements and for carrier particles.

FIG. 1 shows shapes of the mixing element and of carrier particles. Shapes which are solid, respectively have no cavity, are e.g. the pyramids 1 to 4, the spherical polyhedra 5 to 20 as well as 43 to 45 and 74 as well as 76, 58 as well as 79 or 81, the cylinder 21 as well as cylinders 46 and 47 and 53 to 54 with chamfered end faces, the cubes 22, 27 and 31 to 33, the L-shaped angle 23, the U-shaped angle 24, the edge lengths of which are preferably equal, the plates 25 and 26, the cylinders with tapered end faces 37 to 40 and 59 to 63, the cuboids 41 and 42 with pentagonal or polygonal cross-section and flat, parallel end faces, cones and truncated cones 48 to 52, solid hemisphere 55, solid quarter sphere 56, solid ⅔-sphere 57, a spherical shape with protrusions 69 or 70 or spherical shape 72 with protrusions having apertures, or spherical shape 75 or 85 with obtuse protrusions, a half ring 73 with e.g. round cross-section, spherical shape 77 or 82 or 86 and 87 with outwardly projecting spines, spherical polyhedra 80 and 81, and spherical polyhedra 84 with projecting edges between concave surface portions.

Shapes whose walls encompass a cavity are e.g. hollow cylinders 29 and 30, rings 34 to 36 and 88, optionally with serrated protrusions, lattice spheres 64 to 67, which consist of walls arranged in the shape of spherical shells opening up apertures between them, and preferably shapes 28, 68, 78, 83, 89 and 90, which consist of at least one intertwined strip extending in at least two planes arranged at an angle of 60 to 90° to each other and whose outwardly facing surfaces are convexly curved and form an at least sectionally, preferably a continuous spherical rolling surface, wherein the at least one strip encompasses a cavity and opens up apertures between sections of the strip. The intertwined strip may have a circular or angular cross-section. The shape 90 is also known as a rolling knot.

Example: Fluidization of Salbutamol Sulfate on Lactose

As an example of an active ingredient salbutamol sulfate, micronized (SBS, Lusochimica S.p.A, Italy) was used, mixed with lactose for inhalation (InhaLac 120, Meggle, Wasserburg, Germany). The mixing element was made of filamentous polylactide or polyvinyl alcohol (both from Ultimaker B.V, Utrecht, The Netherlands) by melting and metering the melt according to a predetermined pattern by 3D printing or by a photolithographic process from a light polymerizable precursor mass of the polymers in the forms shown as No. 88, No. 89 and No. 90, respectively, in FIG.

1. The size of the mixing elements along their respective maximum extension was 7 mm. The mixing element of shape No. 88 has a central cavity open at two opposing apertures. The mixing element of shape No. 90 has cavities between arcuate walls that are open at a plurality of apertures bordered by the walls. The mixing elements of shape No. 88 and No. 90 have walls whose surfaces opposite the cavity are convexly curved and promote rolling along an inner surface of, for example, a mixing chamber.

The mixing element of shape No. 89 has cavities enclosed by the walls and walls whose surfaces opposite the cavities are convexly curved and promote rolling along an inner surface of, for example, a mixing chamber. Therein, the convexly curved surfaces of the mixing elements of forms No. 90 and No. 89 are continuous.

For the pharmaceutical formulation, the lactose (InhLac 120) and the active ingredient were passed through a 355 μm mesh sieve at 20-25° C., 30-65% relative humidity and then mixed at a speed of 500 rpm (Picomix, Hosokawa Alpine, Augsburg, Germany), twice for 60 s each with one sieving (355 μm mesh) in between.

This mixture of the active ingredient and the lactose was fluidized according to one embodiment, wherein the mixing element was placed in the dispersion chamber and thus in the flow path of the inhaler.

Of the formulation, 20.0 mg each was filled into capsules (Vcaps Plus, size 3, Lonza, Basel) without added mixing element. The capsules were individually placed in a powder inhaler, available under the name "Twister" from Aptar, Louveciennes, France, for measurement of the fine fraction of active ingredient produced after fluidization. The powder inhaler was attached to an impactor through which an air stream generated by a vacuum pump was drawn, the flow rate of which was adjusted by a digital flow meter (model DFM3, Copley Scientific, Nottingham, England) to the flow rate corresponding to a pressure drop of 4 kPa across the inhaler, as determined at the dose collection tube according to Ph. Eur 9.0. A controlled valve was set to an opening time that at the flow rate resulted in an air volume of 4 L, according to Ph. Eur.

The aerodynamic size distribution of particles was determined using a Next-Generation Pharmaceutical Impactor (Apparatus E according to European Pharmacopeia 9.0). Following the analysis, the deposited drug in each section of Apparatus E was dissolved with water after analysis and analyzed separately for drug content by HPLC (RP18 column, detection at 220 nm, mobile phase: 22% acetonitrile, 78% buffer of 2.87 g/L sodium heptasulfonate, 2.50 g/L potassium hydrogen phosphate, pH 3.65, adjusted with 85% orthophosphoric acid, 25° C., flow rate 0.89 mL/min, 10 μL sample volume). Using the Copley Inhaler Testing Data Analysis Software 3.0 (Copley Scientific Ltd.), fine particle mass and fine particle fraction (based on delivered dose) were calculated from aerodynamic particle size distribution (corresponding to PhEur).

It has been shown that, compared to the formulation without a mixing element, a formulation according to the invention that was swirled with a mixing element in the dispersion chamber of the inhaler results in a higher proportion of drug particles with aerodynamic sizes of 5 μm and in a shift in the aerodynamic particle size distribution towards a higher proportion of drug particles <3 μm as well as <2 μm (fine fraction of the dose/fine particle fraction).

The table shows the measured masses and changes in % in relation to the formulation without mixing element.

| shape of mixing element | Fine particle dose [μg] | Fine particles < 5 μm [%] | Fine particles < 3 μm [%] | Fine particles < 2 μm [%] | MMAD [μm] |
|---|---|---|---|---|---|
| Without mixing element | 59 ± 6 | 21.7 ± 2.7 | 19 ± 2.6 | 13 ± 2.2 | 1.847 |
| Shape No. 90 | 71 ± 5 | 24 ± 1 | 21 ± 0.7 | 15 ± 0.25 | 1.759 |
| Cube small | 68 ± 5 | 23 ± 1.2 | 21 ± 1.1 | 15 ± 0.8 | 1.720 |
| Cube medium | 66 ± 1.5 | 22 ± 0.2 | 20 ± 0.1 | 14 ± 0.1 | 1.752 |
| Cube large | 66 ± 5 | 23 ± 1.3 | 20 ± 1.4 | 15 ± 1 | 1.722 |

MMAD = mass median aerodynamic diameter

The small cube has an edge length of 3.8 mm, the medium cube has an edge length of 4.8 mm and the large cube has an edge length of 5.8 mm.

Alternatively, one mixing element per capsule was added to the powdered pharmaceutical formulation of lactose and active ingredient, and this capsule was introduced into the dispersion chamber of the inhaler, where it was subsequently fluidized in the gas stream.

The invention claimed is:

1. A powdered pharmaceutical formulation, comprising a particulate active ingredient and carrier particles to which the particulate active ingredient adheres only to surfaces of the carrier particles, wherein the carrier particles are produced by an additive manufacturing process and have a uniform size of not more than 500 μm of the longest extension and a uniform shape.

2. The powdered pharmaceutical formulation of claim 1, the carrier particles consisting of polylactide, polyglycolide, polylactide-co-glycolide (PLGA), sugar, sugar alcohol, cellulose, hydroxypropyl cellulose, hydroxyethyl cellulose, hydroxypropylmethyl cellulose, gelatin, alginate, agarose, carrageen, or a mixture of at least two of these.

3. The powdered pharmaceutical formulation of claim 1, wherein the uniform shape of the carrier particles is solid with a self-contained surface of a sphere, pyramid, cylinder, three-dimensional oval, cuboid, cube, cone, truncated cone, or polyhedron.

4. The powdered pharmaceutical formulation of claim 3, wherein the uniform shape of the carrier particles comprises protrusions.

5. The powdered pharmaceutical formulation of claim 1, wherein the uniform shape of the carrier particles comprises walls disposed about a cavity and that has at least one aperture open to the cavity.

6. The powdered pharmaceutical formulation according to claim 5, in which the uniform shape of the carrier particles, the walls of which encompass a cavity, are hollow cylinders, rings, optionally with serrated projections, lattice spheres consisting of walls arranged in a spherical shell opening up apertures between them, shapes consisting of at least one strip intertwined in itself, which extends in at least two planes that lie at an angle of 60 to 90° to one another and whose outwardly facing surfaces are convexly curved and form an at least sectionally a continuous spherical rolling surface.

7. The powdered pharmaceutical formulation of claim 5, wherein the uniform shape of the carrier particles, the walls of which encompass a cavity, form shapes consisting of at least one intertwined strip extending in at least two planes that lie at an angle of 60 to 90° to each other, and the outwardly facing surfaces of which are convexly curved and form an at least sectionally a continuous spherical rolling surface, wherein the at least one strip encompass a cavity and opens up apertures between sections of the strip.

8. The powdered pharmaceutical formulation of claim 1, further comprising a mixing element having a size in a first dimension of at least 1 mm and a size in the other two dimensions of at least 50% of the size it has in the first dimension.

9. The powdered pharmaceutical formulation of claim 8, wherein the mixing element comprises walls arranged about a cavity and having at least one aperture open to the cavity.

10. The powdered pharmaceutical formulation of claim 8, wherein the mixing element has walls arranged about a cavity, the walls having at least two apertures arranged on opposing walls and open to the cavity.

11. The powdered pharmaceutical formulation of claim 8, wherein the walls of the mixing element between its outer surface and the cavity have a thickness of no more than 20% of the size of the mixing element in that dimension.

12. The powdered pharmaceutical formulation of claim 8, wherein the mixing element has walls whose surfaces facing the cavity have a total area of no more than 50% of the total area of the at least one aperture spanned by the walls.

13. The powdered pharmaceutical formulation of claim 8, wherein the mixing element has walls formed by one or by at least two interconnected wall sections, each closed on itself about an aperture, extending in at least two planes that lie at an angle of 45° to 90° to each other.

14. The powdered pharmaceutical formulation of claim 8, wherein the mixing element is solid with a self-contained surface.

15. The powdered pharmaceutical formulation of claim 14, wherein the mixing element comprises protrusions extending over the closed surface.

* * * * *